(12) United States Patent
Brouse

(10) Patent No.: US 10,911,891 B2
(45) Date of Patent: Feb. 2, 2021

(54) ALARM ROUTING OPTIMIZATION STRATEGIES IN TARGETED ALARM SYSTEM

(71) Applicant: DRÄGERWERK AG & CO. KGAA, Lübeck (DE)

(72) Inventor: Christopher J. Brouse, Andover, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 931 days.

(21) Appl. No.: 14/896,659

(22) PCT Filed: Dec. 18, 2014

(86) PCT No.: PCT/US2014/071294
§ 371 (c)(1),
(2) Date: Dec. 7, 2015

(87) PCT Pub. No.: WO2016/099520
PCT Pub. Date: Jun. 23, 2016

(65) Prior Publication Data
US 2016/0371449 A1 Dec. 22, 2016

(51) Int. Cl.
*H04W 4/02* (2018.01)
*G08B 25/00* (2006.01)
(Continued)

(52) U.S. Cl.
CPC .......... *H04W 4/023* (2013.01); *G08B 25/001* (2013.01); *G08B 25/003* (2013.01);
(Continued)

(58) Field of Classification Search
CPC .................... G16H 40/20; G06F 19/3406
(Continued)

(56) References Cited

U.S. PATENT DOCUMENTS 5,319,363 A * 6/1994 Welch ............... H04Q 9/00
340/12.3
5,828,835 A * 10/1998 Isfeld ............. G06F 13/387
709/200
(Continued)

FOREIGN PATENT DOCUMENTS

| CN | 102523314 | 6/2012 |
| WO | 2013/093692 A2 | 6/2013 |
| WO | 2013/164721 A1 | 11/2013 |

OTHER PUBLICATIONS

Patent Cooperation Treaty, International Preliminary Report on Patentability for Application No. PCT/US2014/071294, dated Jun. 29, 2017.
(Continued)

*Primary Examiner* — Reginald R Reyes
(74) *Attorney, Agent, or Firm* — Wenderoth, Lind & Ponack, L.L.P.

(57) ABSTRACT

A targeted alarm system is described that includes a network probe for sending test data to terminal devices connected to a network and deriving reliability data of the terminal devices and the network. When a targeted alarm message needs to be sent, the system identifies a targeted terminal device based on the reliability data for sending the targeted alarm message. Related methods, apparatus, and non-transitory computer readable media are also disclosed.

28 Claims, 6 Drawing Sheets

(51) Int. Cl.
*G08B 29/18* (2006.01)
*G16H 40/63* (2018.01)
*H04W 4/90* (2018.01)
*G16H 40/20* (2018.01)
*A61B 5/11* (2006.01)
*G06Q 10/10* (2012.01)
*G08B 26/00* (2006.01)
*G06Q 50/22* (2018.01)
*H04L 29/08* (2006.01)
*A61B 5/00* (2006.01)

(52) U.S. Cl.
CPC ......... *G08B 25/004* (2013.01); *G08B 29/185* (2013.01); *G16H 40/20* (2018.01); *G16H 40/63* (2018.01); *H04W 4/90* (2018.02); *A61B 5/1113* (2013.01); *A61B 5/746* (2013.01); *G06Q 10/1091* (2013.01); *G06Q 50/22* (2013.01); *G08B 26/006* (2013.01); *G08B 26/007* (2013.01); *H04L 67/12* (2013.01); *H04M 2242/04* (2013.01)

(58) Field of Classification Search
USPC .......................................................... 705/2
See application file for complete search history.

(56) References Cited

U.S. PATENT DOCUMENTS

| | | | |
|---|---|---|---|
| 5,920,263 A | 7/1999 | Huttenhoff et al. | |
| 6,364,834 B1 * | 4/2002 | Reuss ................... | G06Q 50/24 600/300 |
| 6,501,975 B2 | 12/2002 | Diab et al. | |
| 6,579,232 B2 | 6/2003 | Sakamaki et al. | |
| 6,671,351 B2 * | 12/2003 | Menard ................ | G08B 25/016 379/38 |
| 6,684,090 B2 | 1/2004 | Ali et al. | |
| 6,687,735 B1 * | 2/2004 | Logston .................... | G06F 8/60 370/486 |
| 6,999,904 B2 | 2/2006 | Weber et al. | |
| 7,066,883 B2 | 6/2006 | Schmidt et al. | |
| 7,138,902 B2 * | 11/2006 | Menard ................ | A61B 5/0002 340/5.53 |
| 7,301,451 B2 * | 11/2007 | Hastings ................ | A61B 5/411 340/539.12 |
| 7,382,247 B2 | 6/2008 | Welch et al. | |
| 7,716,525 B1 * | 5/2010 | Buchko ................... | H04L 12/10 714/22 |
| 7,724,147 B2 * | 5/2010 | Brown ................... | G16H 40/20 340/573.1 |
| 8,471,697 B2 | 6/2013 | Judy et al. | |
| 8,571,893 B2 | 10/2013 | Dashefsky et al. | |
| 8,648,706 B2 * | 2/2014 | Ranjun ................ | G08B 25/008 340/500 |
| 8,648,723 B2 | 2/2014 | Osone et al. | |
| 8,775,196 B2 | 7/2014 | Simpson et al. | |
| 9,218,454 B2 * | 12/2015 | Kiani ................... | G06F 19/3418 |
| 2003/0128125 A1 | 7/2003 | Burbank et al. | |
| 2005/0242928 A1 * | 11/2005 | Kirkeby .................... | G08B 5/22 340/286.07 |
| 2007/0013511 A1 * | 1/2007 | Weiner ............... | G08B 21/0453 340/539.12 |
| 2007/0229249 A1 * | 10/2007 | McNeal ................ | A61B 5/0002 340/524 |
| 2008/0221918 A1 * | 9/2008 | Petersen ................ | G06Q 50/22 705/2 |
| 2009/0045942 A1 | 2/2009 | Schurter | |
| 2009/0046585 A1 * | 2/2009 | Faraj ....................... | H04L 43/50 370/236 |
| 2009/0326340 A1 | 12/2009 | Wang et al. | |
| 2010/0177100 A1 | 7/2010 | Carnes et al. | |
| 2010/0234718 A1 | 9/2010 | Sampath et al. | |
| 2011/0298621 A1 | 12/2011 | Shanbhag | |
| 2011/0316704 A1 | 12/2011 | Nielsen et al. | |
| 2012/0029301 A1 | 2/2012 | Battista | |
| 2012/0126984 A1 | 5/2012 | Gilham et al. | |
| 2012/0127103 A1 | 5/2012 | Qualey et al. | |
| 2012/0130204 A1 | 5/2012 | Basta et al. | |
| 2012/0158996 A1 | 6/2012 | Thaler, III | |
| 2012/0184120 A1 | 7/2012 | Basta et al. | |
| 2012/0232416 A1 | 9/2012 | Gilham et al. | |
| 2012/0323086 A1 | 12/2012 | Hansen | |
| 2012/0327781 A1 * | 12/2012 | Dabbs, III ............. | H04W 4/06 370/241 |
| 2013/0027205 A1 | 1/2013 | Hansen | |
| 2013/0044111 A1 | 2/2013 | VanGilder et al. | |
| 2013/0109927 A1 | 5/2013 | Menzel | |
| 2013/0267873 A1 | 10/2013 | Fuchs | |
| 2014/0085076 A1 | 3/2014 | Carnes | |
| 2014/0159921 A1 | 6/2014 | Qualey et al. | |
| 2014/0350351 A1 | 11/2014 | Halperin et al. | |

OTHER PUBLICATIONS

Patent Cooperation Treaty, International Search Report and Written Opinion for Application No. PCT/US2014/071294, dated Sep. 9, 2015.

Office Action dated Aug. 5, 2020 in Chinese Application No. 201480037575.9, with English language translation.

* cited by examiner

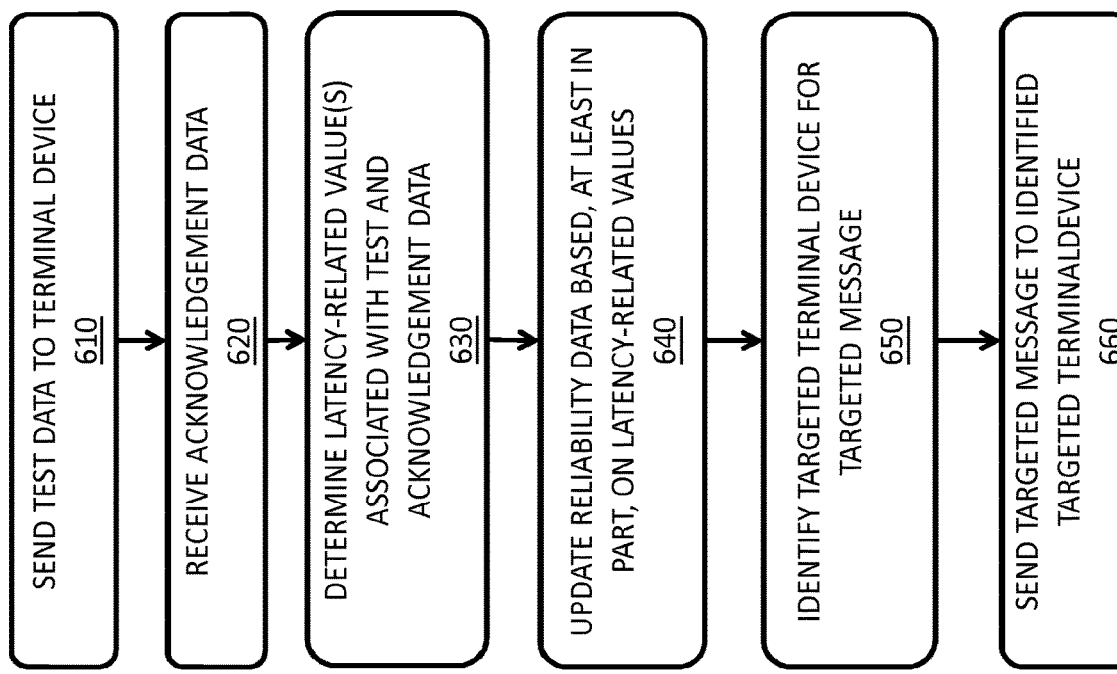

ALARM ROUTING OPTIMIZATION STRATEGIES IN TARGETED ALARM SYSTEM

The present application is a 35 USC § 371 national stage application of International Application No. PCT/US2014/071294, filed Dec. 18, 2014, the entirety of which is incorporated herein by reference.

TECHNICAL FIELD

The subject matter described herein relates to alarm routing monitoring and optimization strategies in a targeted medical alarm system.

BACKGROUND

In a distributed targeted alarm system, there is risk of alarm message delivery failure or delay, which could be harmful to the patient. Delivery failure or delay can emerge at the level of systems integration. Even if individual monitoring hardware and software are perfect, timely deliveries of alarm messages will depend (at least partly) on, for example, the hospital's network infrastructure. Another factor that could cause delivery failure or delay is the terminal devices carried by caregivers that will receive the alarm messages (e.g., iPhones, Android phones, pagers). Different network devices and even caregivers may have different reliability characteristics. For example, a central station hard-wired over Ethernet will likely have a very reliable network connection, while a mobile wireless device may be less reliable. Furthermore, a mobile device connected over a wide area cellular network will have much greater latency than one connected directly to the hospital's internet network. These different possible conditions can create uncertainty in alarm message delivery.

SUMMARY

Variations of the present subject matter are directed to methods, systems, devices, and other articles of manufacture that are provided to alarm routing monitoring and optimization strategies in a targeted medical alarm system.

The present subject matter provides a targeted medical alarm system that includes a network adapter configured to communicate with a plurality of terminal devices over one or more networks. Each of the terminal devices is associated with a respective caregiver. The system also includes one or more data processors and a computer-readable medium storing instructions that when executed by the one or more data processors, performs operations that include sending test data to each of the terminal devices. The operations also include receiving acknowledgement data indicating when the test data was received by the respective terminal device, and determining one or more latency-related values associated with each of the test data and the acknowledgement data; updating reliability data based at least in part on the latency-related values. Based at least in part on the reliability data, a targeted terminal device to which a targeted message is to be sent is identified.

One or more of the following features can be included in any feasible combination. For example, in some variations, the test data comprise one or more test packets. In some variations, the test data is sent periodically. In some variations, the reliability data comprise a reliability map.

In some variations, the operations can also include one or more of: sending the targeted message to the targeted terminal device; receiving one or more response messages generated by each of the terminal devices, and generating one or more statistics for each of the terminal devices based on the one or more response messages; and identifying a secondary terminal device based at least in part on the reliability data and sending the targeted message to the secondary terminal device.

In some variations, the one or more latency-related values include one or more of: a success or failure of acknowledgement, round-trip message latency, a message routing path, and a physical location.

In some variations, the reliability data include one or more of: a current workload data for at least some of the caregivers and the associated terminal devices; a proximity data for at least some of the caregivers and the associated terminal devices; an energy level data for at least some of the caregivers and the associated terminal devices; a historical response data for at least some of the caregivers; and a physical distribution of the caregivers and the associated terminal devices.

In some variations, the one or more statistics include one or more of: a response time, a current location, a typical location, a scheduled activity, and a scheduled location.

In some variations, the targeted terminal device is determined based at least in part on the one or more statistics of each of the terminal devices.

In some variations, the secondary terminal device is identified for each critical message.

In some variations, the server is further configured to generate a report of the reliability data.

In some variations, the targeted device is determined based at east in part on a location distribution of the terminal devices.

In some variations, each of the latency-related values are weighed and combined to generate an overall reliability and latency of each of the terminal devices.

In some variations, the system further includes one or more of the plurality of terminal devices. Each of the terminal devices is configured to generate the acknowledgement data upon receipt of the test data.

The present subject matter also provides a method of targeted medical alarm for implementation by one or more data processors forming part of a least one computing device. The method includes transmitting, by at least one data processor, test data to each of a plurality of terminal devices, and receiving, by at least one data processor, an automatic acknowledgement from each of the terminal devices indicating when the test data were received. Based on the automatic acknowledgement, one or more latency-related values associated with the test data are determined (by at least one data processor), and reliability data based at least in part on the latency-related values are updated. The method also includes identifying, by at least one data processor and based on the reliability data, a terminal device to which a targeted message is to be sent.

One or more of the following features can be included in any feasible combination. For example, in some variations, the test data comprises one or more test packets.

In some variations, the test data is transmitted periodically.

In some variations, the reliability data includes one of more of: a reliability map; a current workload data for at least some of the caregivers and the associated terminal devices; a proximity data for at least some of the caregivers and the associated terminal devices; an energy level data for at least some of the caregivers and the associated terminal devices; a historical response data for at least sonic of the caregivers; and a physical distribution of the caregivers and the associated terminal devices.

In some variations, the method further includes sending the targeted message to the targeted terminal device.

In some variations, the one or more latency-related values include one or more of: a success or failure of acknowledgement, round-trip message latency, a message routing path, and a physical location.

In some variations, the method further includes receiving, by at least one data processor, a response message from a responsive terminal device; and generating, by at least one data processor, one or more statistics of the responsive terminal device based on the response message.

In some variations, the one or more statistics include one or more of: a response time, a current location, a typical location, a scheduled activity, and a scheduled location.

In some variations, the targeted device is determined based at east in part on the one or more statistics of each of the terminal devices.

In some variations, the method further includes identifying, by at least one data processor, a secondary terminal device based at least in part on the reliability data; and sending, by at least one data processor, the targeted message to the secondary terminal device.

In some variations, the secondary terminal device is identified for each critical message.

In some variations, the method further includes generating, by at least one processor, a report of the reliability data.

In some variations, the targeted device is determined based at least in part on a location distribution of the terminal devices.

In some variations, the method further includes weighing and combining, by one or more data processor, each of the latency-related values to generate an overall reliability and latency of each of the terminal devices.

In some variations, the method further includes generating the automatic acknowledgement from each of the terminal devices upon receipt of test data.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or, the like), via a direct connection between one or more of the multiple computing systems, etc.

The subject matter described herein provides many advantages. For example, by providing a system and method that can determine (a) how long it will take for an alarm message to reach a caregiver, and how long will it take that caregiver to respond, (b) the uncertainty in the message latency and caregiver response time, and (c) how a targeted alarm system can mitigate this uncertainty when transmitting life-critical and/or time-critical alarm messages, alarm message delivery failures and delays can be reduced.

BRIEF DESCRIPTION OF THE FIGURES

FIG. 6 shows an example of process flow in accordance with some variations of the current subject matter.

DESCRIPTION

Figure 1:
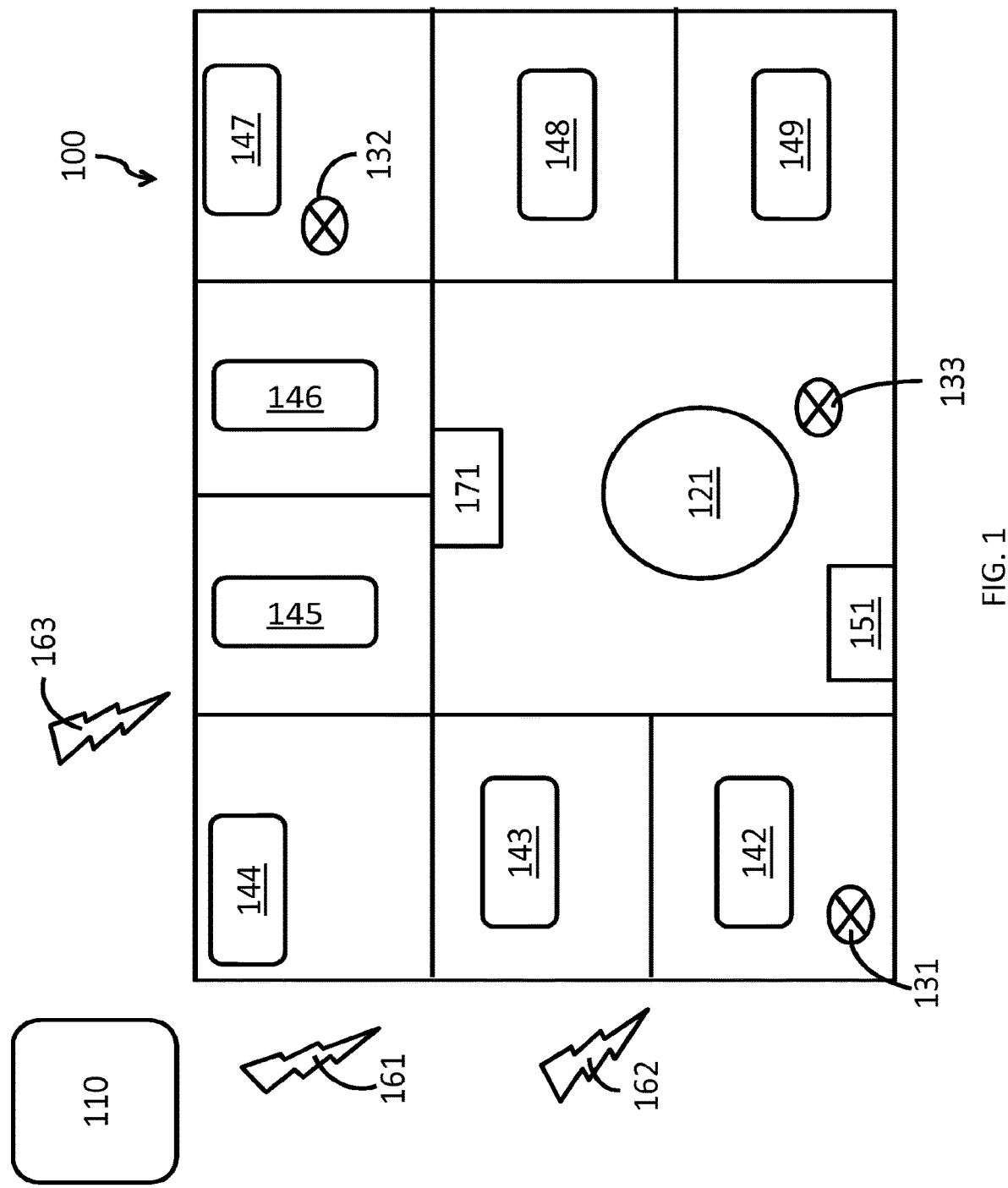
FIG. 1 is a diagrammatic illustration of an example of an environment in accordance with the current subject matter.

FIG. 1 is a diagrammatic illustration of an example of an environment for implementing alarm routing monitoring, and optimization. Here, a targeted medical alarm system 110 is in data communication with terminal devices 131,132, and 133 via one or more of cellular networks 161, 162, 163, and WiFi network 151. The terminal devices are each associated with a respective caregiver, who are caring for one or more patients in room/bed 142-149. The caregiver associated with terminal device 131 is attending to the patient in room/bed 142 while the caregiver associated with terminal device 132 is attending to the patient in room/bed 147. The caregiver associated with terminal device 133 is at the caregiver central station 121, which can be provided with an alarm display system (e.g., connected to a local computer network through a hard-wired data connection like Ethernet). Another alarm display system 171 is also provided in a common area (e.g., in a hallway). The alarm display system 171 can also be connected to the local computer network through a hard-wired data connection like Ethernet, or a wireless data communication (e.g., over WiFi network 151).

Figure 2:
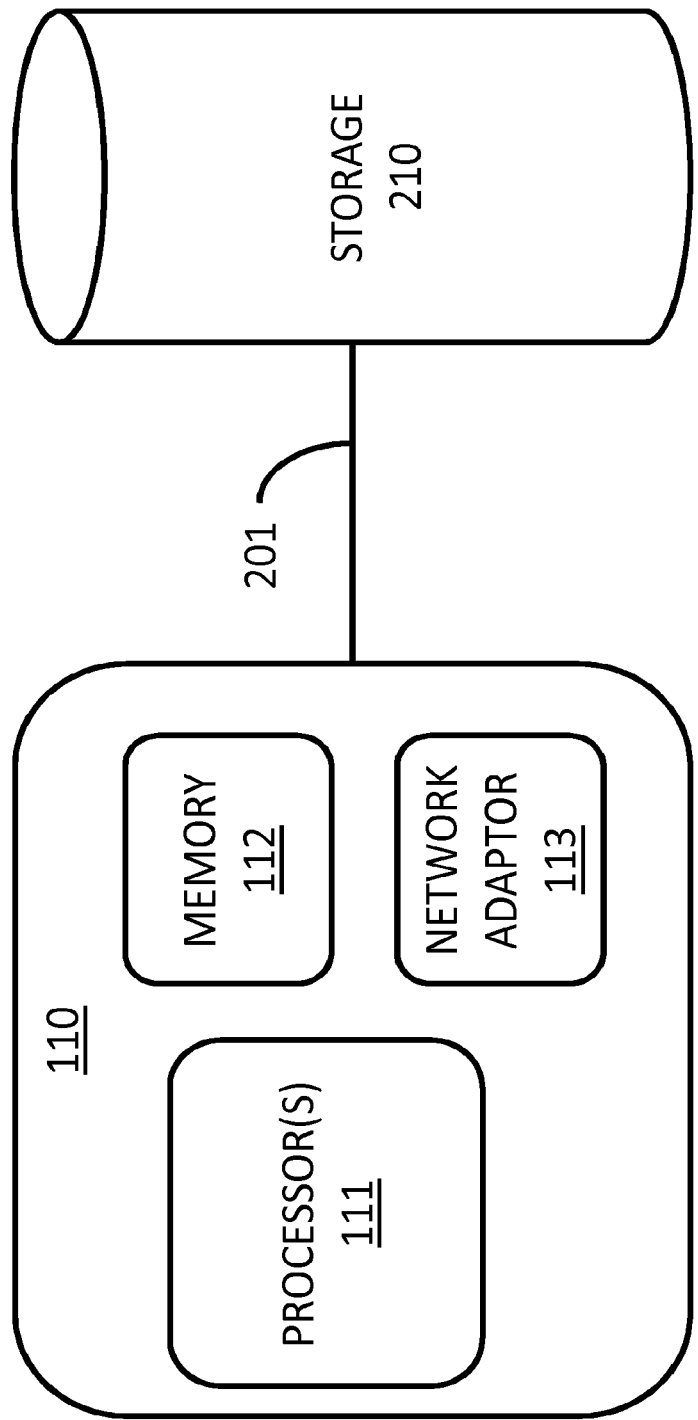
FIG. 2 is a diagrammatic illustration of a system in accordance with some variations of the current subject matter.

FIG. 2 is a diagrammatic illustration of system 110 in accordance with some variations of the current subject matter. In this example, system 110 includes one or more processors 111, memory 112, and network adapter 113. Network adapter 113 is configured to communicate with a plurality of terminal devices (e.g., 131-133). System 110 is in data communication with data storage 210 (e.g., for storing one or more databases containing various data relating to the terminal devices, networks, etc.) via data connection 201. System 110 can also include, for example, input devices such as a keyboard, mouse, and the like, and output devices such as speakers, display, printer, and the like. In some variations, data storage 210 car be implemented as part of the system. Memory 112 and/or storage 210 can include instructions that perform one or more features discussed in this application when executed by one or more processors 111.

In some variations, system 110 can be configured to continuously (automatically) measure network conditions to estimate the reliability of different terminal devices on different branches of the network. For example, terminal device 131 can be connected to cellular network 161, (e.g., a 2G cellular network, through a first provider), terminal device 132 is connected to cellular network 162 (e.g., a 3G cellular network, through a second provider) and WiFi network 151, and terminal device 133 is connected to cellular network 163 (e.g., a 4G cellular network, through a third provider), and system 110 can be configured to monitor and measure network conditions over each cellular network 161-163 and WiFi network 151, In some variations, system 110 can include a network probe configured to send test data to each of the various terminal devices connected to the networks. In some variations, the test data can include test packets, which can be sent, for example, periodically.

In some variations, the terminal devices can be configured to automatically acknowledge receipt of the test data just as they would for an actual alarm message (this can be done, for example, without disturbing the caregiver). The network probe can be configured to log one or more result data including, for example: success or failure of acknowledgement, round-trip message latency, message routing path, and possibility physical location of the terminal device in space.

In some variations, the selection of the target terminal device and/or the time of message could be randomized and/or staggered so as not to overload the network. In some variations, samples are taken frequently enough to gather information with sufficient resolution over time and space. In some variations, after enough samples have been collected, the probe can derive a reliability map of the network. In some variations, the reliability map can be a data set that includes (for example) data representing the reliability of sub-networks, links, and other network components of which the network is comprised. In such a map, some sub-networks and links can be highly reliable and have low latency, while others will be less reliable and have higher latency. Reliability conditions can change over time as network channel and loading conditions change, so in some variations, the map can be (and should be) continuously dynamically updated.

The current subject matter also provides, in some variations, a system configured to predict alarm message latency based on network reliability measurements. In some variations, network reliability can be represented as a graph of probability distributions. In some variations, graph nodes care, for example, represent the terminal devices, and links between nodes can, for example, represent the network infrastructure. The network probe can be configured to find nodes and links to have certain probability distributions of latency (in the event of failure, infinite latency). In some variations, the targeted alarm system can be configured to estimate the total latency, for example, by combining the latency distributions through the graph. The result would be probabilistic, represented, for example, by a random variable with a probability distribution. Statistics could be calculated from the random variable, including, for example, one or more of: mean, median, mode, variance, skew, kurtosis, and higher order measures of uncertainty.

References will be made now to FIGS. 3-5, which show examples of the latency distribution, and probability distributions. These figures are provided for illustrative purposes only, and do not limit the current subject matter.

Figure 3:
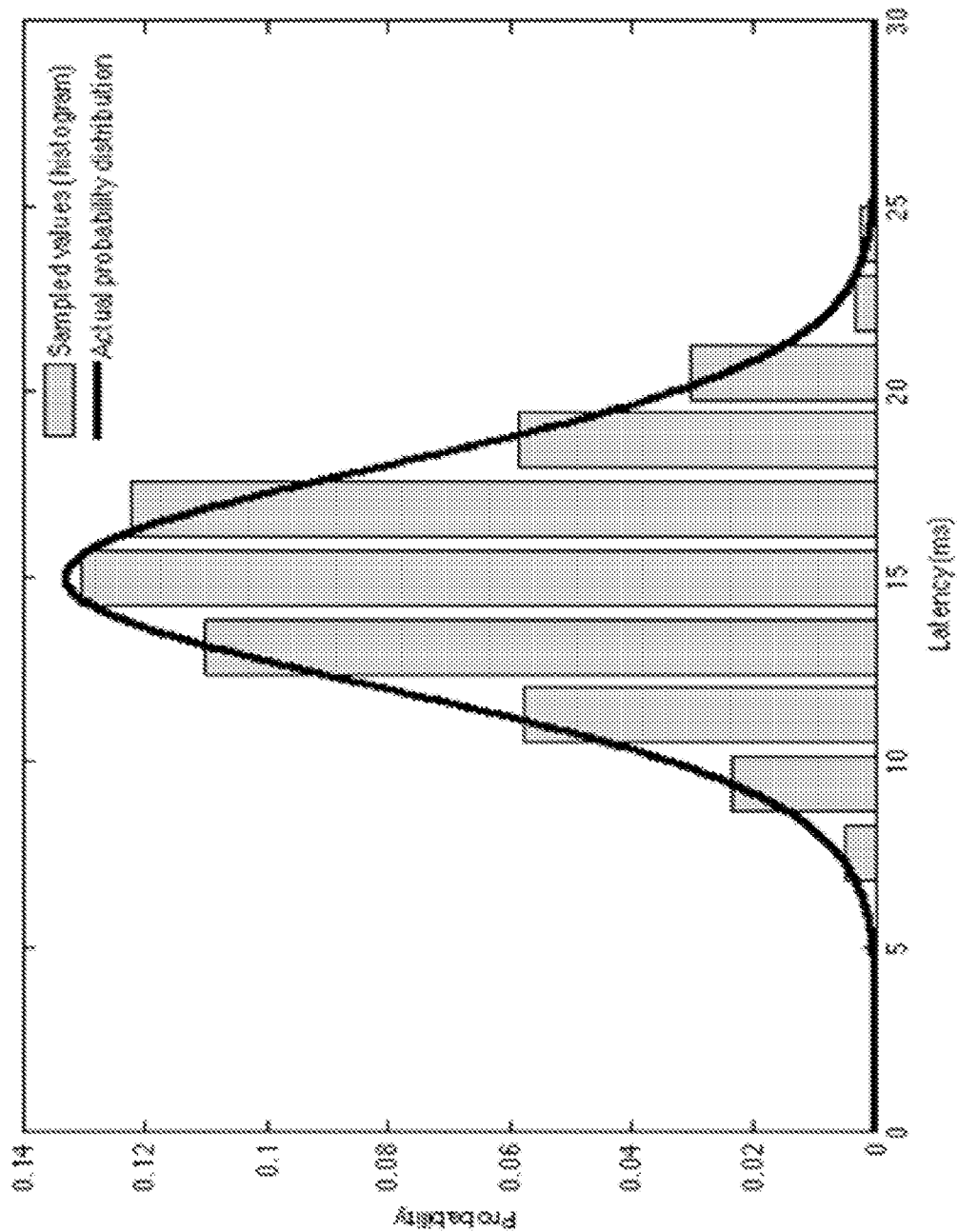
FIGS. 3-5 are graphs showing examples of the latency distribution, and probability distributions.

FIG. 3 shows an example of how a large collection of latency samples can be used to estimate a probability distribution. The system can be configured to sample a device's latency periodically and records the value. As the values are collected, they can be represented in a histogram (the histogram shown in FIG. 3 is normalized; that is, the frequency values are divided by the total number of samples). As the number of samples becomes very large, the histogram tends to an underlying probability distribution, probability density function (PDF). The PDF can then be used by the system to estimate the statistics of the device's latency.

Figure 4:
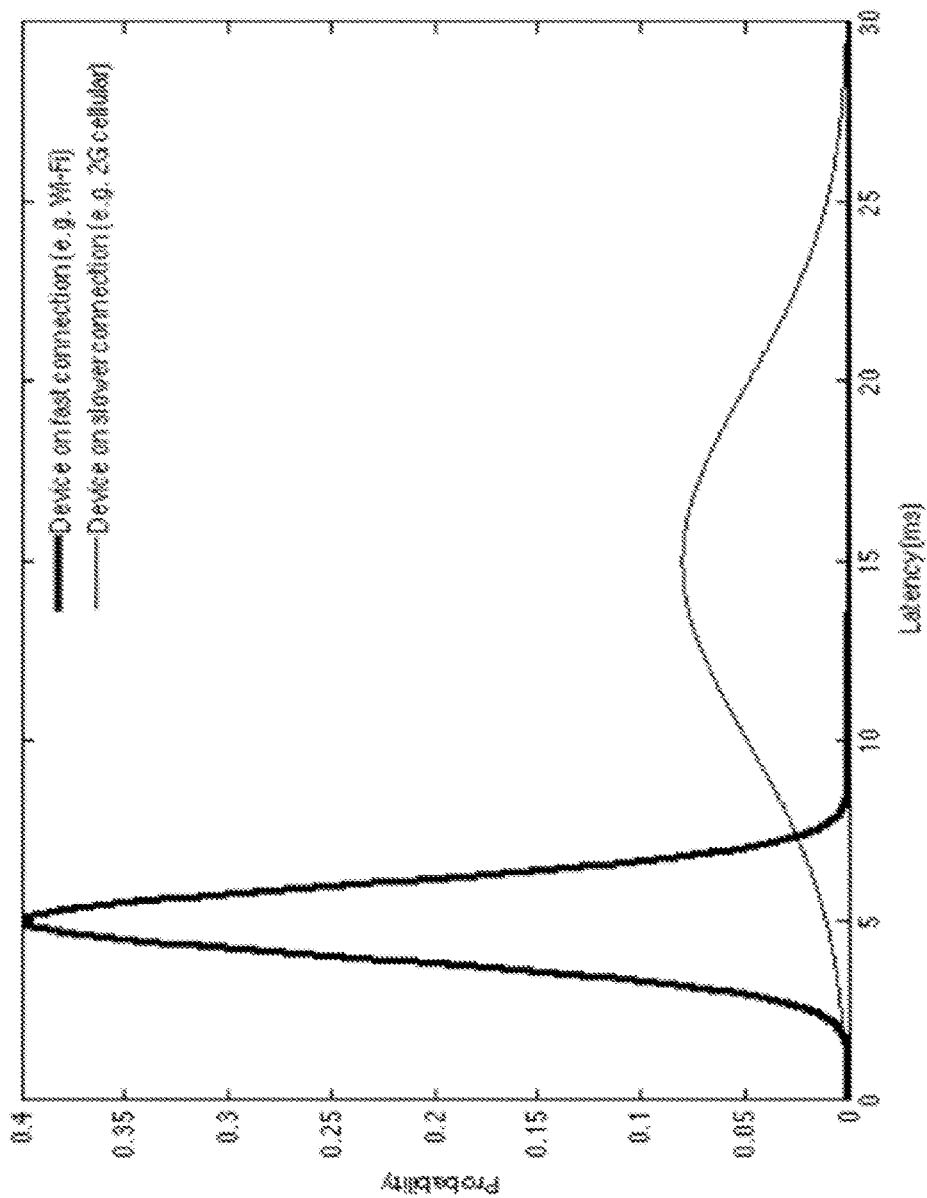

FIG. 4 shows an example of the probability distributions of latency for two different devices. One device is connected to the hospital's internal Wi-Fi network, and the other on a legacy 2G cellular network. These data have been collected from historical latencies measured during automatic sampling. The Wi-Fi connected device has a lower mean latency (5 ms vs. 15 ms), which means that on average it will receive the message more quickly. It also has a smaller variance (1 ms$^2$ vs. 25 ms$^2$), which means that its latency is more stable and predictable. The Wi-Fi connected device is expected to have a shorter latency and is thus a better target for a time-sensitive message (all else being equal).

Figure 5:
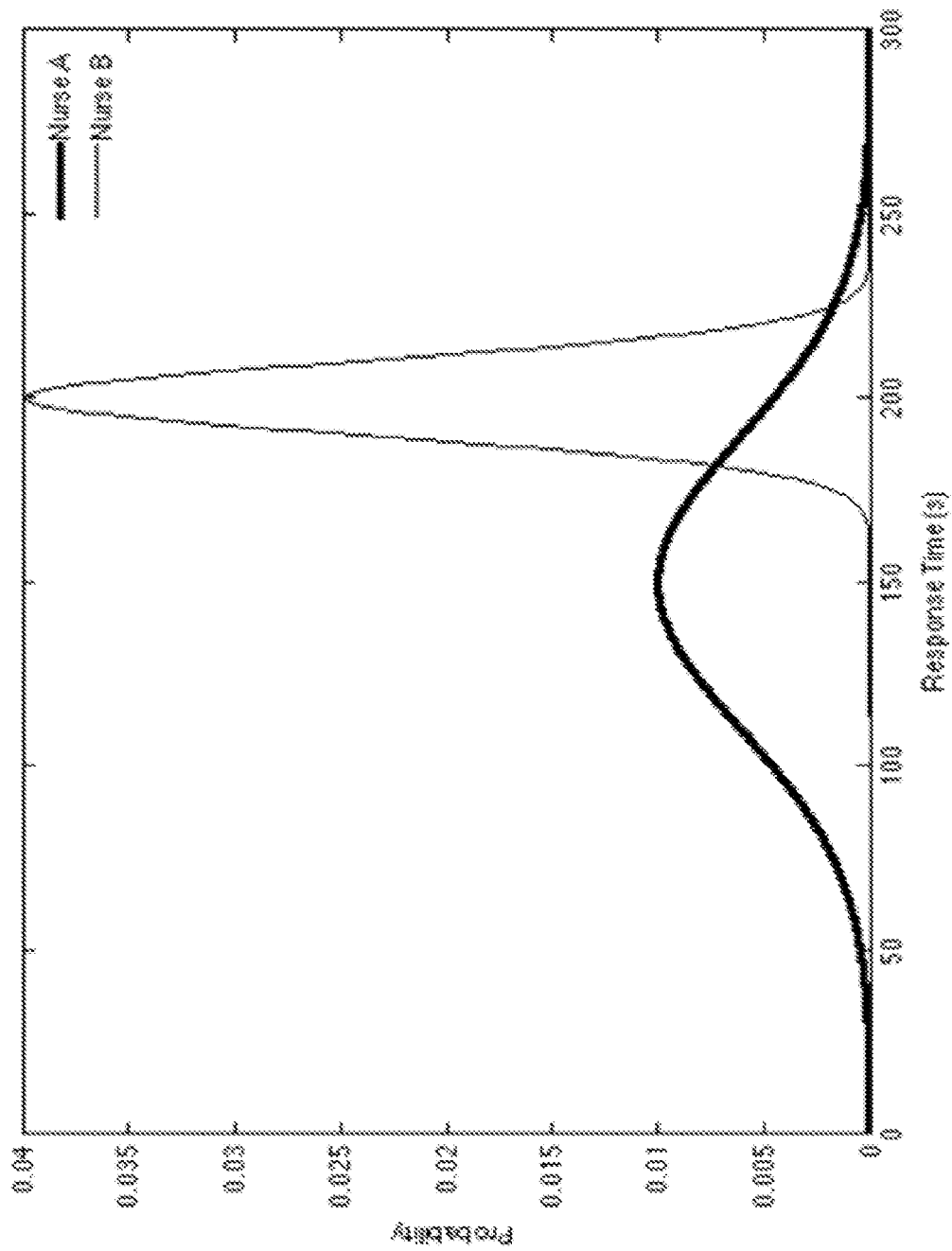

FIG. 5 shows the probability distributions of response time for two different nurses. These data have been collected from historical response times to previous targeted alarms. Nurse A has a lower mean latency (150 s vs. 200 s), which means that on average s/he will respond to a message more quickly. However, Nurse A has a larger variance (1600 s$^2$ vs. 100 s$^2$), which means his/her response time is less predictable. Nurse A is expected to respond more quickly to the message, but there is a chance s/he may take much longer to respond. In certain situations this may be acceptable. In other situations, a more stable/predictable response time may be more desirable than a quicker average response time. The system may choose Nurse A or B based on its requirements for the given message.

The probability distributions can be combined together to arrive at a total response time distribution. Individual parameters may include the device latency given its current location and network connection, the individual caregiver's innate response time, the caregiver's time since the start of his/her shift, the caregiver's current workload, and the travel time from the caregiver's current location. Probability density functions (PDFs) as shown in FIGS. 4, 5, and 6 can be combined by convolving them. The convolution operator is a standard mathematical technique known to those skilled in the art, and can easily be implemented on a computer. For a full treatment of the combinations of probability distributions, see e.g. Springer M.D. 1979, "The Algebra of Random Variables," John Wiley & Sons, New York (the contents of which are incorporated herein by reference).

In some variations, the targeted medical alarm system can be further configured to track one or more statistics on the individual caregivers, including, for example one or more of:

A. Response times: historical response times to alarm messages can be used to estimate the caregiver latency. This latency can be estimated, for example, as a factor independent of the network infrastructure and messaging device used.

B. Current location: If real-time location tracking is available, the system can be configured to track it.

C. Typical locations: If real-time location tracking is unavailable, the system can be configured to use typical assignment locations from the caregiver's schedule as approximations for expected latency calculations.

D. Scheduled activities and locations: If a caregiver is assigned to different care areas at different times or days, the system can be configured to track this information to predict caregiver location.

In some variations, the targeted medical alarm system can be configured to use feedback from the probe's estimated statistics of the network, devices, and caregivers to intelligently identify one or more recipients for each alarm message. For example, when a monitor detects a critical condition in a patient that requires an immediate response (e.g., asystole or ventricular fibrillation), the targeted alarm system can be configured to employ, for example, a routing table that can include an escalation path (having, for example, one or more of primary, secondary, tertiary, etc.)

caregivers responsible for responding to the alarm to route the critical message in an efficient way that minimizes delivery failure and/or delay. In some variations, the system can be configured to minimize its routing path to elicit the most rapid response possible.

In some variations, the targeted medical alarm system can be configured to select (identify) or reject a terminal device/caregiver based on estimated network latency and reliability. For example, the reliability map may indicate that the primary caregiver is in an unreliable branch of the network. The probe map may have this information from, for example, real-time location tracking, scheduled caregiver activities, or statistics of historical locations for this particular caregiver. In response, the targeted alarm system can be configured, for example, to re-route the alarm to a secondary caregiver who is more likely to receive the high priority alarm quickly. This can be repeated, in some variations, to be re-routed to a tertiary, or additional layers of caregivers depending on estimated network latency and reliability. In some variations, the system can include a threshold value (e.g., maximum latency permitted) in identifying or rejecting a terminal device/caregiver.

FIG. 6 shows an example of process flow in accordance with some variations of the current subject matter. At 610, the system sends test data to a terminal device 310. The terminal device is configured to generate acknowledgement data, including when the test data was received, and send the acknowledgement data to the system (received by the system at 620). The system determines one or more latency-related values associated with the test and acknowledgement data at 630, and updates (e.g., generates and stores) reliability data that are based, at least in part, on the one or more latency-related values at 640. When the system needs to send a targeted alarm message (e.g., a critical care message), the system identifies a targeted terminal device (with an associated caregiver) for the targeted message at 650, which is based, at least in part, on the reliability data. At 660, the system sends the targeted message to the identified targeted device.

In some variations, the alarm system can be configured to select (identify) or reject a terminal device/caregiver based on estimated device latency and/or reliability. For example, the probe map may indicate that the primary caregiver's device has a high latency (e.g., connected to a 2G cellular network). In response, the targeted alarm system can be configured to re-route the alarm to a secondary (or a tertiary, etc.) caregiver who is more likely to receive the high priority alarm quickly.

In some variations, the alarm system can be configured to select (identify) the optimum terminal device/caregiver based on the caregiver's current workload. The scheduling statistics may indicate that the primary caregiver is currently occupied on another alarm or assigned to a different high priority action, and may be too busy to react quickly. In response, the targeted alarm system can be configured to re-route the alarm to the secondary (or tertiary etc.) caregiver who is currently unoccupied, or less busy, and thus able to respond more quickly. In some variations, the system can be configured to send the alarm message to an already-occupied caregiver only if the alarm is of higher priority than the caregiver's current task.

In some variations, the alarm system can be configured to select (identify) the optimum caregiver based on, for example, proximity to the patient needing care. Using the real-time location tracking of all caregivers, the system can be configured to determine that for example, the tertiary caregiver is in closest proximity to the patient. Proximity measures can be, for example, simple linear distances, or can take into account a map of the care area and the travel path required to reach the patient. In response, the targeted alarm system can be configured to re-route the alarm to the tertiary caregiver (for example) who is able to respond more quickly.

In some variations, the alarm system can be configured to select (identify) an optimum caregiver based on energy level, estimated from the time since the start of the caregiver's shift. For example, the system can be configured to record, for example, the number and/or the type of tasks the caregiver has performed during a particular shift. Based on this information, the system can be configured to route the alarm message to a fresh caregiver at the start of his/her shift (or who has performed fewer and/or lesser tiring tasks), who is more likely to have higher energy levels and is more likely to respond quickly to the alarm.

In some variations, the alarm system can be configured to select (identity) an optimum caregiver based on historical response rates and/or times. For example, the system can be configured to reject a primary caregiver who often fails to response to alarm messages in the past (e.g., does not notice his/her phone vibrating), in favor of a more responsive secondary caregiver.

In some variations, the system car be configured to maintain a physical distribution of caregivers to prepare for unexpected future alarms. For example, the system can be configured to keep track of the physical locations of individual caregivers, and the larger distribution of the caregiver population. The system can be configured to target the alarms in such a way as to help ensure the caregivers remain physically distributed across care areas. If most caregivers were to become concentrated all in one care area, it would leave some patients more at risk of a longer response to a critical event.

In some variations, the system can be configured to employ one or more (including all) factors and variations described above, for example, weighing them to identify a target caregiver for sending the alarm message. For example, the reliability and/or latency of one or more (including all) elements in the system (e.g., network, device, caregiver) can be combined to estimate the overall reliability and latency of each caregiver at a given point in time. The system can be configured to select (identify) the caregiver with the highest reliability and/or lowest latency at the particular time required for the particular alarm condition, and routes the alarm message to him/her.

In some variations, the system can be configured to generate a report including one or more of, for example, reliability, latency, and other statistics to help identify one or more weak points in the targeted alarming system. Such reports could allow, for example, the hospital administration, or technicians, to improve unreliable parts of the network, upgrade terminal devices that do not perform well as alarm recipients, and device caregiver management strategies to improve schedule, physical distribution, workflow, and more.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items, For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do no represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A targeted medical alarm system comprising:
   a network adapter configured to communicate with a plurality of terminal devices over one or more networks, each of the terminal devices being associated with a respective caregiver;
   one or more data processors; and
   a computer-readable medium storing instructions that when executed by the one or more data processors, performs operations comprising:
   transmitting test data to each of the terminal devices;
   receiving acknowledgement data indicating when the test data was received by the respective terminal device;
   automatically measuring network conditions of the one or more networks by determining, for at least one of the terminal devices, one or more latency-related values associated with each of the test data and the acknowledgement data, the latency-related values including a message latency;
   automatically updating reliability data based at least in part on the latency-related values including the message latency, the reliability data including at least one of (i) historical latency-related values for the at least one of the terminal devices and (ii) historical response data for a respective caregiver associated with the at least one of the terminal devices, the historical response data including one or more response times of the respective caregiver to one or more previous targeted messages;
   identifying a targeted terminal device to which a current targeted message is to be sent based at least in part on the updated reliability data including the at least one of (i) the historical latency-related values for the at least one of the terminal devices and (ii) the historical response data for the respective caregiver associated with the at least one of the terminal devices, thereby reducing delay or failure of delivery of the current targeted message; and
   sending the current targeted message to the targeted terminal device.

2. A method of targeted medical alarm for implementation by one or more data processors forming part of at least one computing device, the method comprising:
> transmitting test data to each of a plurality of terminal devices;
> receiving an automatic acknowledgement from each of the terminal devices indicating when the test data were received; and
> automatically measuring network conditions of the one or more networks by determining, for at least one of the terminal devices, one or more latency-related values associated with the test data, the latency-related values including a message latency;
> automatically updating reliability data based at least in part on the latency related values including the message latency, the reliability data including at least one of (i) historical latency-related values for the at least one of the terminal devices and (ii) historical response data for a respective caregiver associated with the at least one of the terminal devices, the historical response data including one or more response times of the respective caregiver to one or more previous targeted messages;
> identifying a targeted terminal device to which a current targeted message is to be sent based at least in part on the updated reliability data including the at least one of (i) the historical latency-related values for the at least one of the terminal devices and (ii) the historical response data for the respective caregiver associated with the at least one of the terminal devices, thereby reducing delay or failure of delivery of the targeted current message; and
> sending the current targeted message to the targeted terminal device.

3. The method according to claim 2, wherein the test data comprises one or more test packets.

4. The method according to claim 2, wherein the test data is transmitted periodically.

5. The method according to claim 2, wherein the reliability data comprises a reliability map.

6. The method according to claim 2, wherein the reliability data includes a current workload data for the respective caregiver associated with the at least one of the terminal devices.

7. The method according to claim 2, wherein the reliability data includes a proximity data for the respective caregiver associated with the at least one of the terminal devices.

8. The method according to claim 2, wherein the reliability data includes an energy level data the respective caregiver associated with the at least one of the terminal devices.

9. The method according to claim 2, wherein the reliability data includes the historical response data for the respective caregiver associated with the at least one of the terminal devices.

10. The method according to claim 2, wherein the reliability data includes a physical distribution of the respective caregiver associated with the at least one of the terminal devices.

11. The method according to claim 2, wherein the one or more latency-related values include one or more of: round-trip message latency, a message routing path, and a physical location.

12. The method according to claim 2, further comprising:
> receiving a response message from a responsive terminal device; and
> generating one or more statistics of the responsive terminal device based on the response message.

13. The method according to claim 12, wherein the one or more statistics include one or more of: a response time, a current location, a typical location, a scheduled activity, and a scheduled location.

14. The method according to claim 12, wherein the targeted device is determined based at least in part on the one or more statistics of each of the terminal devices.

15. The method according to claim 2, further comprising:
> identifying a secondary terminal device based at least in part on the reliability data; and
> sending the current targeted message to the secondary terminal device.

16. The method according to claim 15, wherein the secondary terminal device is identified for each critical message.

17. The method according to claim 2, further comprising generating a report of the reliability data.

18. The method according to claim 2, wherein the targeted device is determined based at least in part on a location distribution of the terminal devices.

19. The method according to claim 2, further comprising weighing and combining each of the latency-related values to generate an overall reliability and latency of each of the terminal devices.

20. The method according to claim 2, further comprising generating the automatic acknowledgement from each of the terminal devices upon receipt of the test data.

21. A targeted medical alarm system comprising:
> a network adapter configured to communicate with a plurality of terminal devices over one or more networks, each of the terminal devices being associated with a respective caregiver;
> one or more data processors; and
> a computer-readable medium storing instructions that when executed by the one or more data processors, performs operations comprising:
>> transmitting data to each of the terminal devices;
>> receiving acknowledgement data indicating when the transmitted data was received by the respective terminal device;
>> automatically measuring network conditions of the one or more networks by determining, for at least one of the terminal devices, one or more latency-related values associated with each of the transmitted data and the acknowledgement data, the latency-related values including a message latency;
>> automatically updating reliability data based at least in part on the latency-related values including the message latency, the reliability data including at least one of (i) historical latency-related values for the at least one of the terminal devices and (ii) historical response data for a respective caregiver associated with the at least one of the terminal devices, the historical response data including one or more response times of the respective caregiver to one or more previous targeted messages;
>> identifying a targeted terminal device to which a current targeted message is to be sent based at least in part on the updated reliability data including the at least one of (i) the historical latency-related values for the at least one of the terminal devices and (ii) the historical response data for the respective caregiver associated with the at least one of the terminal devices; and
>> sending the current targeted message to the targeted terminal device.

22. The targeted medical alarm system according to claim 21, wherein the transmitted data includes at least one of test data and actual data.

23. The targeted medical alarm system according to claim 22, wherein the test data includes one or more test packets.

24. The targeted medical alarm system according to claim 22, wherein the test data is transmitted periodically.

25. The targeted medical alarm system according to claim 22, wherein the actual data includes an alarm message.

26. The targeted medical alarm system according to claim 1, wherein the reliability data includes both of (i) the historical latency-related values for the at least one of the terminal devices and (ii) the historical response data of the respective caregiver associated with the at least one of the terminal devices.

27. The method according to claim 2, wherein the reliability data includes both of (i) the historical latency-related values for the at least one of the terminal devices and (ii) the historical response data of the respective caregiver associated with the at least one of the terminal devices.

28. The targeted medical alarm system according to claim 21, wherein the reliability data includes both of (i) the historical latency-related values for the at least one of the terminal devices and (ii) the historical response data of the respective caregiver associated with the at least one of the terminal devices.

* * * * *